United States Patent [19]

Machida et al.

[11] Patent Number: 5,023,020
[45] Date of Patent: Jun. 11, 1991

[54] METHOD FOR SUPPLYING AROMAS, APPARATUS THEREFORE AND FACILITIES PROVIDED WITH SAME

[75] Inventors: Hiroji Machida; Michiaki Asano; Yozo Watanabe; Tomoya Tokuhiro; Hiroshi Satoh; Motoyuki Iwahashi; Norihiro Yamaguchi; Koshin Kikuchi; Hiroaki Watanabe, all of Tokyo, Japan

[73] Assignee: Shimizu Construction Co., Ltd., Tokyo, Japan

[21] Appl. No.: 494,853

[22] Filed: Mar. 14, 1990

Related U.S. Application Data

[63] Continuation of Ser. No. 204,373, Jun. 9, 1988, abandoned.

[30] Foreign Application Priority Data

Jun. 10, 1987 [JP] Japan .................. 62-144334
Nov. 10, 1987 [JP] Japan .................. 62-283629

[51] Int. Cl.⁵ .............................. B01F 3/04
[52] U.S. Cl. .................... 261/18.1; 261/30; 261/DIG. 48; 261/DIG. 65; 239/305; 422/124
[58] Field of Search ........ 261/30, DIG. 48, DIG. 65, 261/18.1; 239/305; 422/124, 20

[56] References Cited

U.S. PATENT DOCUMENTS

| | | | |
|---|---|---|---|
| 1,758,552 | 5/1930 | Allen et al. | 239/305 |
| 2,555,047 | 5/1951 | Logne | 239/305 |
| 2,614,820 | 10/1952 | Boydjieff | 422/124 |
| 2,686,944 | 8/1954 | Gubelin | 239/305 |
| 3,298,674 | 1/1967 | Gilbertson | 261/30 |
| 3,298,674 | 1/1967 | Gilbertson | 422/124 |
| 3,711,023 | 1/1973 | Smith . | |
| 3,924,810 | 12/1975 | Otterstetter | 239/305 |
| 4,081,139 | 3/1978 | Migliozzi | 239/305 |
| 4,087,495 | 5/1978 | Umehara | 261/DIG. 68 |
| 4,601,886 | 7/1986 | Hudgins | 422/124 |
| 4,603,030 | 7/1986 | McCarthy | 422/124 |
| 4,629,604 | 12/1986 | Spector | 422/124 |
| 4,695,434 | 9/1987 | Specter | 261/DIG. 65 |

FOREIGN PATENT DOCUMENTS

| | | |
|---|---|---|
| 535375 | 11/1980 | Australia . |
| 0004039 | 9/1979 | European Pat. Off. . |
| 0123746 | 7/1984 | European Pat. Off. . |
| 0144992 | 6/1985 | European Pat. Off. . |
| 2573283 | 5/1986 | France . |

OTHER PUBLICATIONS

American Heritage Dictionary, Apr. 1982, p. 1266.

*Primary Examiner*—Tim Miles
*Attorney, Agent, or Firm*—Cushman, Darby & Cushman

[57] ABSTRACT

A method for supplying aromas to a space includes the steps of retaining a plurality of aromatic materials in respective reservoirs, selecting at least one of the aromatic materials according to a predetermined timetable determined on the basis of activities of people in the space at each time, diffusing a predetermined amount of the selected aromatic material in air to obtain aromatized air, and sending the aromatized air into the space. The apparatus for supplying aromas includes a receptor having plural aromas, a controller for controlling the receptor to select one stated aroma from the plural aromas in the receptor according to an influence on people by the stated aroma at a stated time in a day, and a ventilator for supplying an air containing the stated aroma. A facility provided with an apparatus for supplying aromas includes plural zones with each being provided with the apparatus, and plural routes for connecting the zones to each other.

11 Claims, 9 Drawing Sheets

| TIME | | CONCEPT | AROMA | EFFECTS |
|---|---|---|---|---|
| 6:00 | WAKE-UP | FRESH | LEMON | STIMULATING MENTALLY ACTIVATING CIRCULAR SYSTEM |
| 8:00 | BREAKFAST | DELICIOUS | LAVENDER | STIMULATING APPETITE OR RELAXING |
| | WORKING (OFFICE) | EFFICIENTLY | LEMON LAVENDER MINT ROTATED AT (AN INTERVAL OF) AN HOUR | STIMULATING MENTALLY REFRESH, EFFECT OF ANTI-MIGRAIN |
| 17:00 | REST | COMFORTABLE | LAVENDER | RELIEVING STRESS OR ANXIETY |
| 23:00 | SLEEPING | | | |

METHOD FOR SUPPLYING AROMAS, APPARATUS THEREFORE AND FACILITIES PROVIDED WITH SAME

This is a continuation of application No. 07/204,373, filed June 9, 1988, which was abandoned upon the filing hereof.

BACKGROUND OF THE INVENTION

1. Field of the Invention

This invention relates to a method for supplying aromas and an apparatus therefore which can be utilized on occasions where the aromas are supplied to various facilities such as homes for the old, hospitals, offices, buildings, stations, houses, or the like, or into various vehicles such as trains, subways, motor cars, airplanes, or the like. Further, this invention relates to facilities provided with the apparatus above.

2. Prior Art

Recently, aromas are becoming the object of public attention as ways for enriching life. Examples of methods for supplying the aromas to such rooms as sitting rooms, toilets and the like include a method using a box-type aromatic which can be put on the table, etc. In the method, the aromas are used for masking odors or smells which are caused by odorants such as cigarettes, cigars, ordures and the like. The stronger the aroma is the more preferable the aromatic is for masking the odor.

Some aroma are known to have substantial physiological effects. For instance, some aroma diffused by lemon have stimulant effects or act as cures for drowsiness because they excite people mentally, and moreover they activate the people circulatory system. Also, some aroma diffused by lavender have effects of relieving stress, anxiety, or the like, and further have antidepressive effects because they relax tension. Further some aroma diffused by rosemary and the like have orexigenic and relaxative effects. In addition, "phytoncide", which means aromas or compounds diffused by trees or woods, are known to have effects of sterilization against harmful bacteria or virus, and therefore have effects of restoration of good health to people.

In conventional methods, such aromas are utilized without availing of their effects on people mentally, unfortunately.

SUMMARY OF THE INVENTION

Accordingly, it is an object of the present invention to provide a method for supplying aromas so as to make use of the valuable physiological effects of the aromas.

Another object of the present invention is to provide an apparatus which is adequate to carry out effectively the method for supplying aromas of this invention.

A further object of the present invention is to provide a facility which has the apparatus for supplying aromas of this invention so as to define spaces which are adequate to obtain a physical or mental health effect.

According to a first aspect of this invention, there is provided a method for supplying aromas comprising the steps of:

(a) retaining a plurality of aromatic material separately in respective reservoirs;

(b) selecting at least one of the aromatic materials according to a predetermined timetable determined on the basis of activities of people in the space at each time;

(c) diffusing a predetermined amount of the selected aromatic material in air to obtain aromatized air; and (d) sending forth the aromatized air into the space.

Many investigations have been made concerning influences by aroma, and thereby many acknowledgments are made as follows.

(1) Aromatic materials having a stimulant activity include essential oils such as Japanese mint oil, eucalyptus oil, lemon oil, citronella oil, salvia oil, thyme oil, clove oil, rosemary oil, and the like, extracts such as onions, garlic, and the like, acids such as formic acid, acetic acid, ethers such as ethyl formate, propyl formate, ethyl acetate, normal propyl acetate, buthyl acetate, heptyl acetate, nonyl acetate, menthyl acetate, isomenthyl acetate, amyl nitrite, trimethylcyclohexanol, allyl sulfide, and the like.

(2) Aromatic materials having an hypnotic activity include essential oils such as jasmine oil, camomile oil, neroli oil, and the like, alcohols such as nonyl alcohol, decyl alcohol, phenylethyl alcohol, and the like, and ethers such as methyl carbonate, ethyl carbonate, and the like.

(3) Aromatic materials, which have an appetite-depressing activity, include essential oils such as armoise oil, rosemary oil, eucalyptus oil, and the like, compounds such as ethylphenyl acetate, guaiacol, indole, cresol, thiophenol, p-dichlorobenzen, p-methylquinoline, isoquinoline, pyridine, organic amines, camphor, mercaptan, ammonia, hydrogen sulfide, and the like.

(4) Aromatic materials, which have an appetite-stimulating activity, include essential oils such as perilla oil, marjoram oil, thyme oil, laurel oil, juniperus oil, lemon oil, nutmeg oil, ginger oil, onion oil, garlic oil, and the like, and compounds such as l-carvone, estragon oil, elemi oil, and the like.

(5) Aromatic materials, which have antidepressive activities or activities of relieving anxiety, include essential oils such as lavender oil, bergamot oil, lemon oil, marjoram oil, rosemary oil, peppermint oil, rose oil, jasmine oil, nutmeg oil, cinnamon oil, clove oil, ginger oil, and compounds such as citral, citronellal, borneol, linalol, geraniol, nerol, rhodinol, and the like.

According to a second aspect of this invention, there is provided an apparatus for supplying aromas, the apparatus comprising a receptor having plural aromas, a controller for controlling the receptor to select one stated aroma from the plural aromas in said receptor according to an influence on people by the stated aroma at a stated time in a day, and a ventilator for supplying an air containing the stated aroma.

According to a third aspect of this invention, there is provided a facility provided with the apparatus for supplying aromas of the present invention, the facility including plural zones each being provided with the apparatus, and plural routes for connecting the zones each other.

DESCRIPTION OF PREFERRED EMBODIMENT OF THE INVENTION

Figure 1:
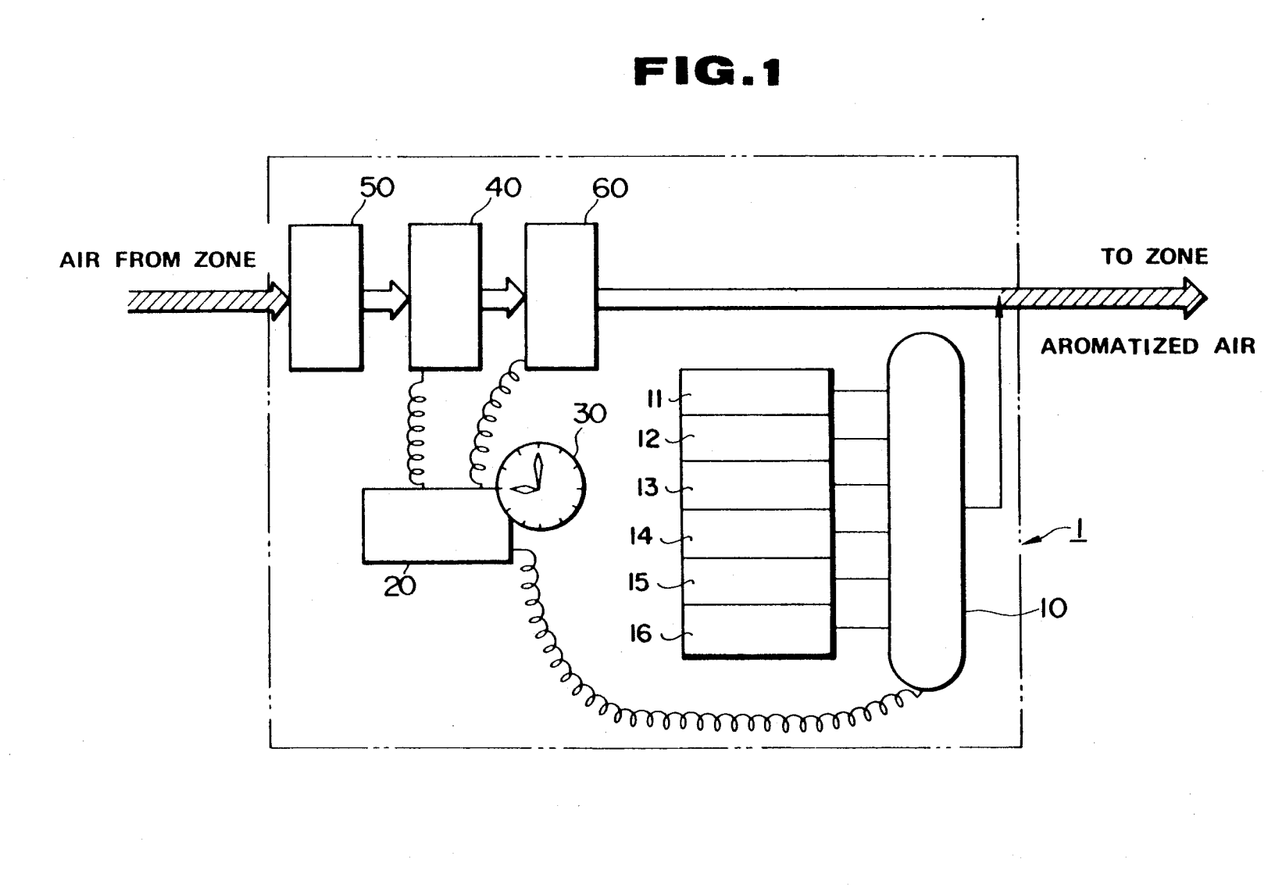
FIG. 1 is a diagram illustrating an embodiment of the apparatus for supplying aromas of the present invention.

Referring to FIG. 1, there is illustrated a diagram of an embodiment of the apparatus for supplying aromas of the present invention. Reference numeral 1 denotes an apparatus for supplying aromas to a zone (not shown) in which the apparatus is disposed, and the apparatus comprises a receptor 10 having six reservoirs or containers 11-16 which are respectively filled with a liquid aroma, a controller 20 for controlling the receptor 10 to thereby select only a stated container from the six containers so as to diffuse only one aroma, and a ventilator (not shown) for supplying air containing the aroma or aromatized air to the zone. In this case, the receptor 10 retains six different aromas in the containers 11-16 thereof. The amount of the aroma supplied to the zone is adjusted to a predetermined value by the controller 20. Such controller 20 is connected with a timer 30 in order that the controller 20 controls the receptor 10 according to a timetable. The timetable is predetermined according to a data where a stated aroma influences people, or a data where the influence by the stated aroma peaks at the stated time of day.

The controller 20 is connected with an exchanger 40 for exchanging heat with air which is discharged from the zone through an air filter 50, and is connected with a humidifier 60 for humidifying the dry air flowing from the exchanger 40. The air filter 50 provides deodorants such as activated charcoals and the like in order to remove odors from the air discharged from the zone. Also, the humidifier 60 is connected with the zone, and therefore the air discharged from the zone returns to the zone after circulating through the zone, the air filter 50, the exchanger 40, and the humidifier 60. In the air circuit, the passage between the zone and the air filter 50 is connected with a passage out of the receptor 10.

In thus described apparatus 1, a predetermined aroma is selected from the six aromas of the receptor 10 by opening the container containing the selected aroma. Such selection of the aroma is carried out on basis of the aforesaid influence thereof on people at a predetermined time.

On the other hand, odor is removed from the air discharged from the zone by the air filter 50. The air passed through the air filter 50 exchanges heat thereof by the exchanger 40, and is humidified by the humidifier 60.

The thus-obtained air is mixed with the above selected aroma within the passage between the zone and the humidifier 60, and the air containing aroma returns to the zone by the aforesaid ventilator. Therefore, the air in the zone becomes refreshed and comfortable because it contains an aroma having a good influence on people at the predetermined time.

Figure 2:
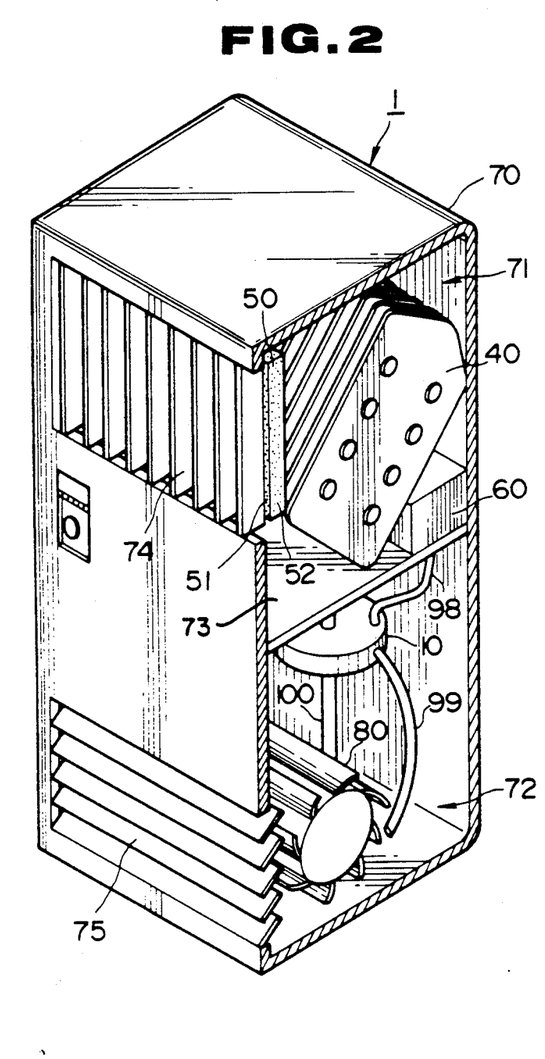
FIG. 2 is a perspective side view of an embodiment of the apparatus for supplying aromas of the present invention, with parts broken away.
Figure 3:
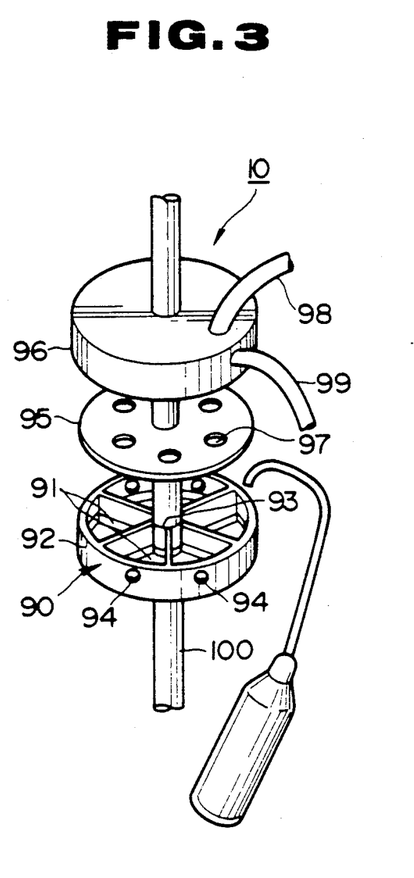
FIG. 3 is an exploded view of an example of the receptor having the apparatus of FIG. 2.

Referring to FIGS. 2 and 3, there is illustrated an embodiment of the apparatus for supplying aroma as shown in FIG. 1. The apparatus 1 is housed in a housing 70 which can be disposed in the above described zone. The housing 70 has a cubic shape, and has two separate spaces or an upper space 71 and a lower space 72 which are separated by a middle wall 73, and further has an upper window 74 and a lower window 75 which are respectively formed at the upper and lower portion of the front face thereof.

In the upper space 71, the exchanger 40 and the humidifier 60 are disposed at a corner defined by the middle wall 73 and a rear wall of the housing 70. The air filter 50 is disposed on the peripheral edge of the upper window 74. In this embodiment, the air filter 50 comprises a sheet-like prefilter 51 in contact with the peripheral edge of the window 74 and a deodorant sheet 52 made of activated charcoal which is fixedly secured to the face of the prefilter 51 directed away from the window 74.

In the lower space 72, a sirocco fan 80 is disposed beside the lower window 75 on the bottom of the housing 70, and the receptor 10 is vertically disposed beside a rear wall of the housing 70. As seen from FIG. 3, the receptor 10 comprises a cylindrical vessel 90 which includes a circular bottom 91, a peripheral wall 92 defined along the peripheral edge of the bottom 91, and a central aperture 93 opened at the central portion of the bottom 91. A vertical shaft 100 is fixedly inserted in the central aperture 93 of the vessel 90. The vessel 90 has six containers defined by six walls extending radially from the central aperture 93 to the inner face of the peripheral wall 92, and further has six apertures 94 opened to every container in order to link the container to the outer space of the vessel 90. A circular sheet or a packing 95 is fixedly secured to the upper portion of the vessel 90 so as to be coaxial therewith, and a cylindrical covering 96 is loosely superposed on the packing 95 on the upper portion thereof so as to be coaxial therewith. The packing 95 has an aperture which is opened at the central portion thereof in order that the shaft 100 is fixedly inserted in the aperture, and further has six apertures 97 which are opened at the peripheral portion thereof corresponding to the six containers of the vessel 90. The covering 96 is larger in a caliber than the vessel 90, and has a central aperture in order that the shaft 100 is loosely inserted in the aperture. Such covering 96 is connected with the humidifier 60 by a pipe 98. Namely, one end of the pipe 98 extends through the middle wall 73 to the humidifier 60 placed in the upper space 71, and another end thereof extends through the top wall of the covering 96 and the apertures 97 of the packing 95 to the containers of the vessel 90. In addition, one end of a pipe 99 extends through the peripheral wall of the covering 96 and the aperture 97 of the vessel 90 to the containers, and another end of the pipe 99 extends to the position beside the plural fins of the aforesaid sirocco fan 80.

In the receptor 10, the vessel 90 and the packing 95 can be rotated together about the shaft 100 by rotating the shaft 100 by an actuator (not shown) such as a step motor and the like, without rotating the covering 96. When the aroma 11 is selected from the six aromas 11 to 16 in the receptor 10, the vessel 90 is rotated until the pipe 98 is in fluid communication with the pipe 99 through the container providing the aroma 11.

In thus described apparatus 1, the air of the aforesaid zone is introduced into the air filter 50 through the upper window 74, and odors removed therefrom, the heat of the air is exchanged by the exchanger 40, the air is humidified by the humidifier 60, and further is sent to the receptor 10 through the pipe 98. Subsequently, the air is introduced into the container for the stated aroma through the aperture 97 of the packing 95 to thereby be mixed with the predetermined aroma, and the thus obtained air containing aroma or aromatized air is sent to the position beside the sirocco fan 80 through the aperture 94 of the vessel 90 and the pipe 99. Therefore, the aromatized air returns to the zone through the lower window 75 by the fan 80.

Figure 4:
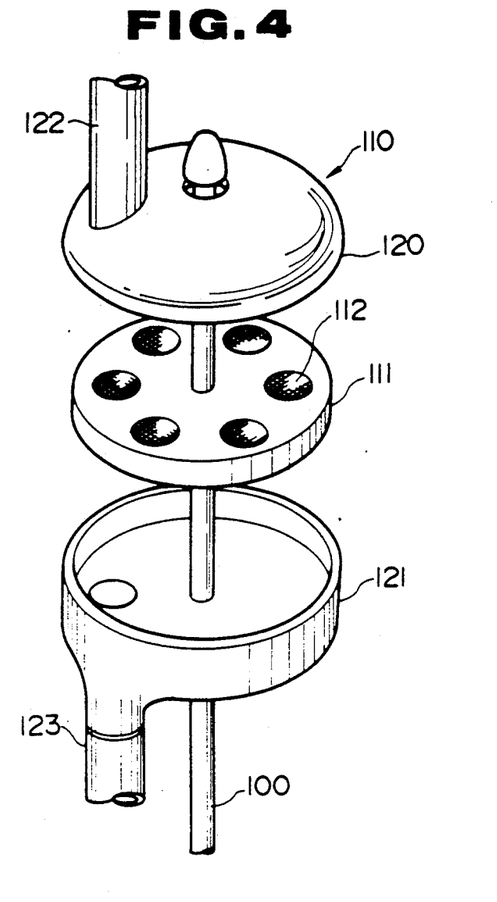
FIG. 4 is an exploded view of another example of the receptor as shown in FIG. 3.
Figure 5:
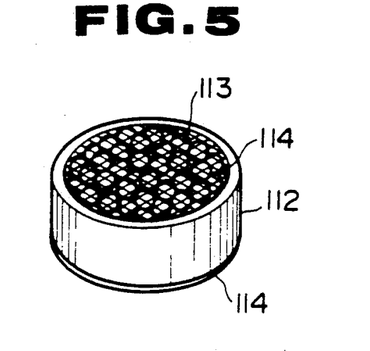
FIG. 5 is a perspective view of an example of a cassette having an aroma used in the receptor of FIG. 4.

Referring to FIGS. 4 and 5, there is illustrated another preferred example of the receptor of the apparatus of the present invention. As seen from FIG. 4, the receptor 110 comprises a circular plate 111 having six circular apertures opening at regular intervals at the marginal portion along the peripheral edge thereof, and six aromatic cassettes 112 having a cylindrical shape which are respectively housed in the apertures of the circular plate 111. The receptor 110 has a central aperture opening at the central portion thereof in order to fixedly insert the aforementioned shaft 100 therein. Also, the receptor 110 is interposed between an upper mask 120 and a lower mask 121 which are fixedly superposed on each other. Two masks 120 and 121 have a substantially hemispherical shape together, and further have respectively a central aperture opening at the central portion thereof in order to receive loosely the shaft 100 therein. A pipe 122 is a member for introducing air into the receptor 110. One end of the pipe 122 is fixedly secured to the curved wall of the upper mask 120, and another end thereof is connected with the above described humidifier 60. Also, a pipe 123 is a member for discharging air from the receptor 110, and one end of the pipe 123 is fixedly secured to the curved wall of the lower mask 121, and another end thereof is extended to the position beside the sirocco fan 80. Further the pipe 123 is fluid communication with the pipe 122 through the cassette 112 in a circular plate 111.

As seen in FIG. 5, plural beads 113 having the aroma adhered to the faces thereof are housed in the cassette 112, and are retained in the cassette 112 by a pair of screen sheets 114 which are disposed on the opposite ends of the cassette 112.

In the apparatus 1 of FIGS. 4 and 5, one stated aroma is selected from the six aromas. Namely, the circular plate 111 is rotated through the shaft 100 by the above described actuator until the predetermined cassette 112 is interposed between the pipe 122 and 123. When the predetermined cassette 112 is interposed between the pipes 122 and 123, the air discharged from the humidifier 60 is introduced into the cassette 112 through the pipe 122 and the upper mask 120. The air is mixed with the aroma of the predetermined cassette 112, and the air containing the selected aroma or aromatized air is sent to the position beside the sirocco fan 80 through the pipe 123. Therefore, the aromatized air returns to the zone through the lower window 75 by the fan 80.

Figure 6:
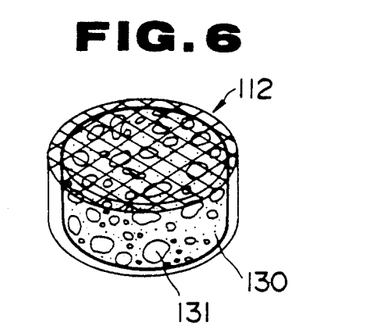
FIG. 6 is a perspective view of another example of a cassette for use in the receptor of FIG. 4.

As seen from FIG. 6, a cylindrical sponge 130 containing the liquid aroma 131 may be housed in the cassette 112 instead of the beads 113.

Figure 7:
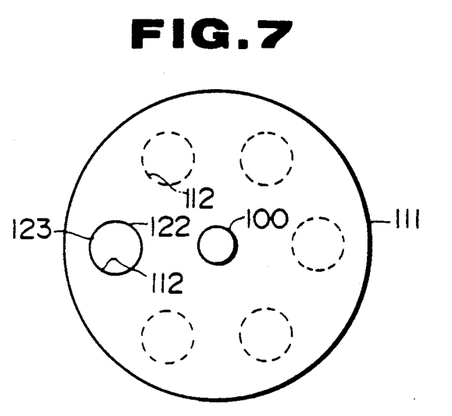
FIG. 7 is a plan view of the receptor of FIG. 4, showing a cassette thereof in its opened position.
Figure 8:
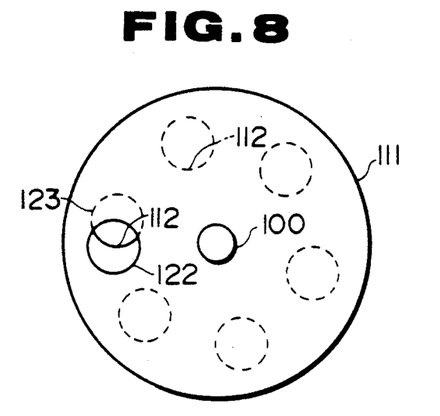
FIG. 8 is a view similar to FIG. 7 but showing the cassette in its half-opened position.

In the apparatus 1 of FIGS. 4 and 5, or 6, the content of the aroma supplied to the zone can be controlled by adjusting the area of the cross-sectional portion on which one end of the pipe 122 and one end of the pipe 123 are superposed on each other through the cassette 112. Namely, when the content is increased to the maximum level, both the pipes 122 and 123 are completely superposed on each other as shown in FIG. 7. Also, when the content is decreased lower than the maximum level, the pipes 122 and 123 are partially superposed on each other as shown in FIG. 8.

Figure 9:
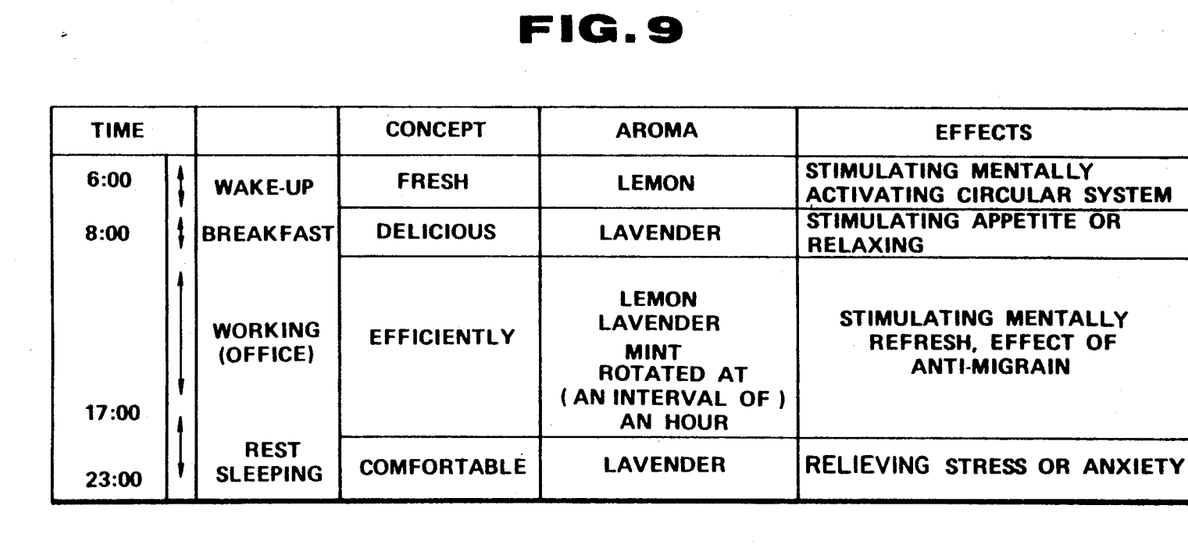
FIG. 9 is a diagram showing the experimental results where aromas are diffused in a room while alternating the types of the aromas and the concentration thereof in the air.

As for the apparatus 1 illustrated in FIGS. 2 to 8, the apparatus 1 may be placed in houses or offices as the aforesaid zone. In this case, the apparatus 1 can be controlled depending on the program which produces a desirable model of life as shown in FIG. 9, so that the kind of aroma is changed when the predetermined time is passed. As seen from FIG. 9, at home, the aroma diffused by lemon is selected as aromatic material at a wake-up time in the morning, and the aroma diffused by rosemary is selected at a breakfast time. In office, an aroma is selected from the group consisting of aromas diffused by lemon, lavender and mint at an interval of an hour in rotation while working. At home, the aroma diffused by lavender is selected before sleeping. Thus, The aroma is determined on the basis of acitvities of people in the space or zone.

Figure 10:
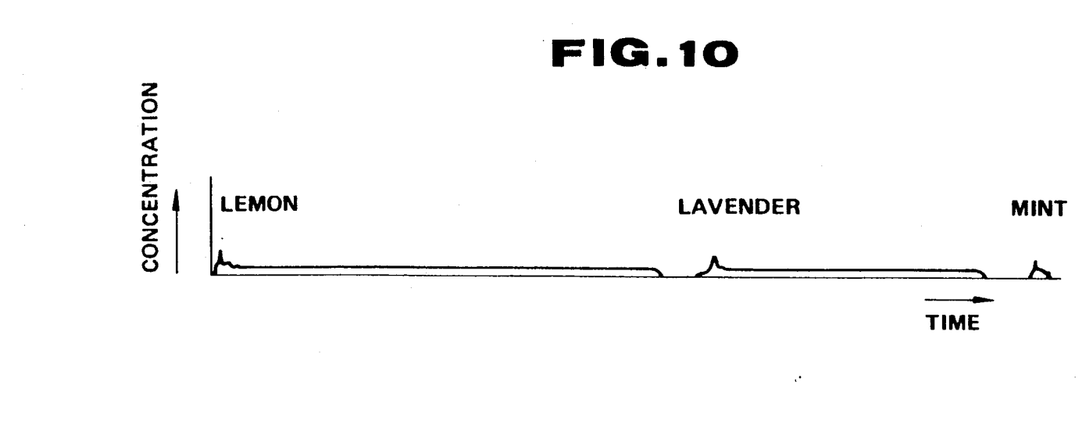
FIG. 10 is a graph showing the relation between the time and the concentration of the aromas in the experimental results of FIG. 9.

In addition, the concentration of the aroma diffused in the zone is preferably controlled by a manner as shown in FIG. 10. According to the manner illustrated in FIG. 10, concentration of the aroma is ordinarily controlled so as to be at the minimum detectable level of human sensing. However, after the aroma is changed, or after the preset time is passed, the concentration thereof becomes preferably beyond the threshold value by increasing the content of the aroma supplied for a short time. As the result of controlling the concentration, the presence of the aroma can be made aware, and further mental or physical effects, on which the aroma has influences, can be elevated to a high level.

Figure 11:
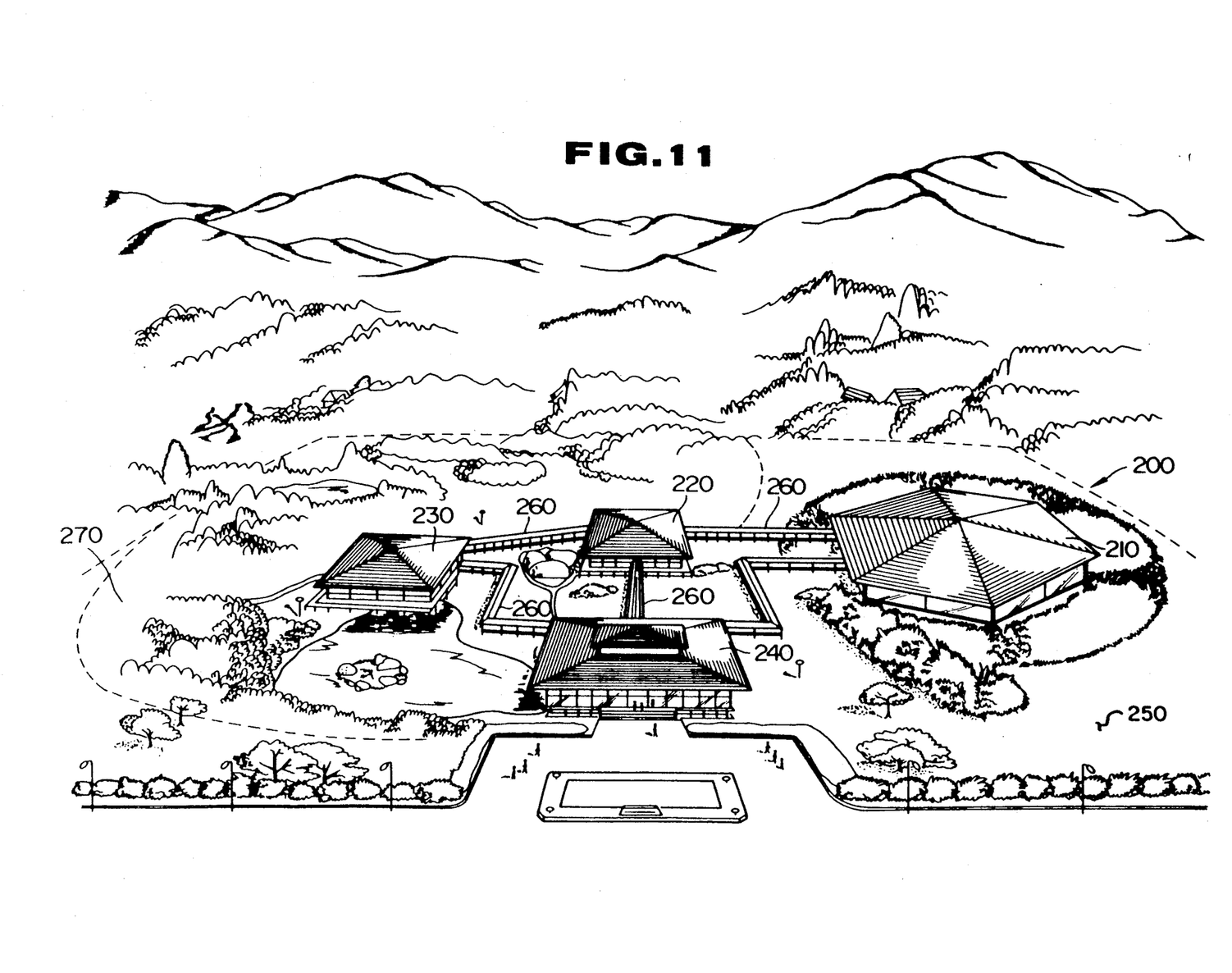
FIG. 11 is a perspective view of an embodiment of the facility for recuperation of the present invention, provided with the apparatus of FIG. 2.

FIGS. 11 to 15 show an embodiment of a facility of the present invention. Reference numeral 200 denotes a facility comprising a zone for health 210, a zone for relaxation and beauty 220 provided with the apparatus 1, a zone for heart 230 provided with the apparatus 1, and a hall 240. The zones 210, 220, and 230, and the hall 240 are constructed on grounds 250, and are connected with plural routes 260 each other as shown in FIG. 11.

A "car-park" 270 having trees and flowers is landscaped on the grounds 250 spreading around the zones 210, 220, and 230, and the hall 240.

Figure 12:
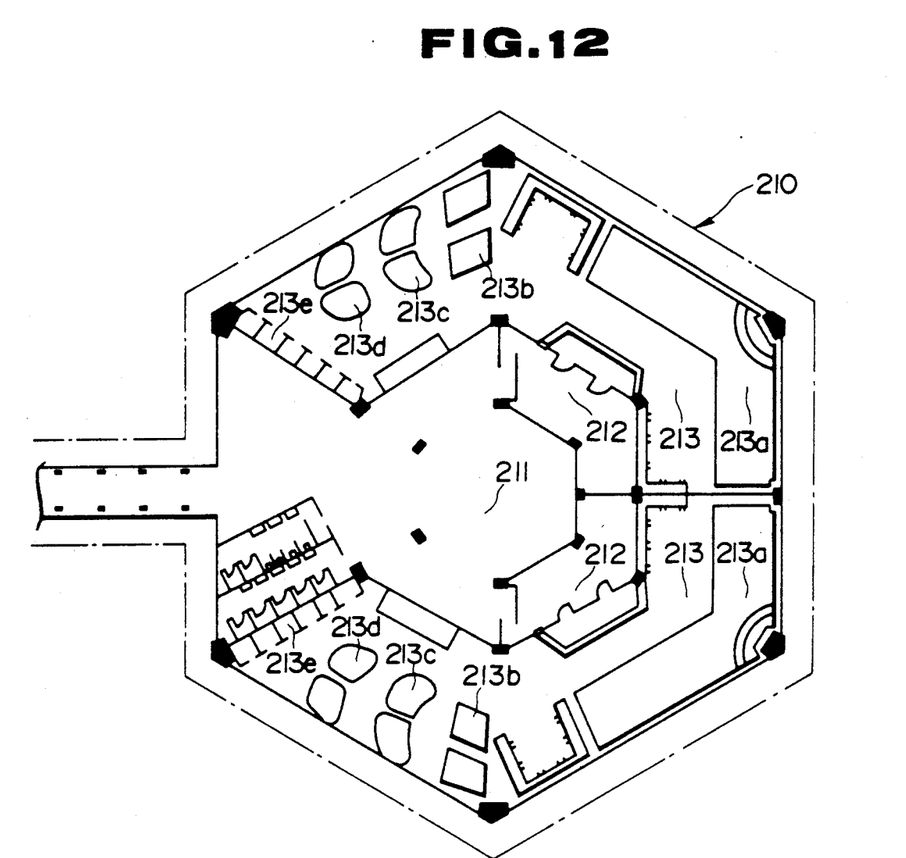
FIG. 12 is a sectional view taken on a horizontal plane, showing a zone for health in part of the facility of FIG. 11.

The zone for health 210 has a hex cross section in a horizontal direction. A booth 211 for selling essential oils used before the bath, or after the bath, eau de cologne, powders for the bath, waters for drinking, and the like is disposed in the central portion of the zone for health 210, and a dressing room 212 is disposed around the booth 211. Further two bath rooms 213 for male and female are disposed in the portion around both the booth 211 and the dressing room 212 as shown in FIG. 12.

The bath room 213 has a big bath 213a filled with water for spa such as weak-alkaline water etc., a perfumed bath 213b, a small bath 213c filled with essential oils, a small bath 213d for a thalasso-therapy, and a perfumed shower bath 213e.

Essential oils extracted from natural materials such as orange, lemon, bergamot, lavender, rosemary, basil, peppermint, camphor, eucalyptus, citron, plum, and the like, or fragrances such as menthol, cineole and the like, or a combination thereof are used as aromatic materials in the perfumed bath 213b. The perfumes such as essential oils and the like are, if necessary, mixed with a surface active agent in order to be water-soluble. The perfumed bath 213b can mentally excite the guests or users with olfactory sense to thereby elevate their feelings.

Figure 13:
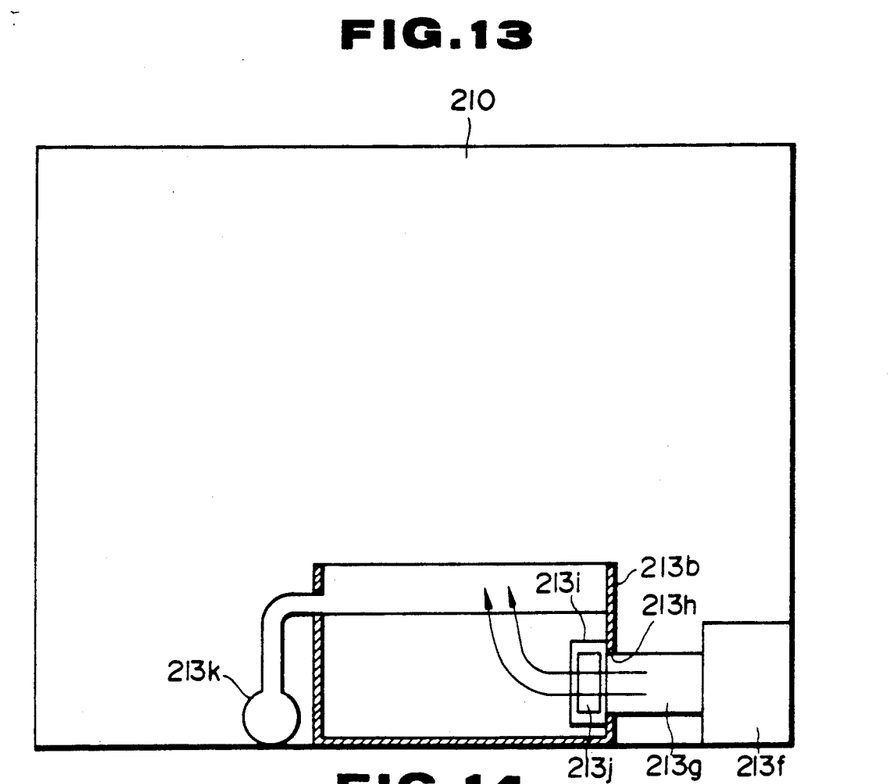
FIG. 13 is a sectional view taken on a vertical plane, showing an apparatus for supplying aromas disposed within a bath of the zone for health of FIG. 11.

The perfumed bath 213b may be used as a bubble bath as shown in FIG. 13. In this case, a bubbler 213f for supplying the bubbles into the tub is located by the perfumed bath 213b, and they are connected by a pipe 213g. An aperture 213h is opened at the portion of the peripheral wall of the tub where one end of the pipe 213g is adhered, and a holder 213i is fixedly disposed on the marginal portion along the aperture 213h. A cassette 213j for supplying the perfume to the hot water in the tub is housed in the holder 213i. In the perfumed bath 213b, the perfume is introduced into the tub by the influence of the bubbles, so that the perfume is diffused into the zone for health 210 from the surface of the water of the tub. Also, water overflowing the tub is received by a pipe 213k, and returned to the tub after filtration.

The small bath 213c filled with aromatic materials such as essential oils which can stimulate directly the skin of the user thanks to the materials to thereby recuperate the user. Also, the essential oils used in the bath 213c may be applied to all or a part of the body of the user before bathing. In the bath 213c, only the essential oils used are recovered from the water overflowing the tub in such a manner such as in the aforesaid perfumed bath 213b.

The water used in the small bath 213d for the thalasso-therapy includes at least components of sea and extracts of seaweeds or marine plants, and therefore the bath 213d can promote the metabolism of the user, or elevate the effects of keeping warm because minerals such as iodide etc., are dissolved in the water of the bath.

The perfume used in the perfumed bath 213b can dissolved in the water of the perfumed shower bath 213e.

The peripheral wall of the zone for health 210 is made of transparent glasses, and a flower bed (not shown) is landscaped in the car-park 270 spreading around the zone 210, and therefore the flower bed can be looked at through the transparent wall of the zone 210. For instance, when lavender flowers are landscaped in the flower bed, and the perfume of lavender is premeated in the zone 210, the product of the olfactory sense is multiplied by the visual sensation.

Further a big screen (not shown) may be disposed in the car-park 270 instead of the flower bed. In this case, the images such as woods, flowers, scenery, and the like relating to the perfume permeated in the zone 210 are projected on the big screen.

The aforesaid apparatus 1 of FIGS. 2 and 3 is disposed in the zone 220 for relaxation and beauty. Such zone 220 is preferably filled with the predetermined aroma at the predetermined time a day owing to the apparatus 1 controlled depending on the time schedule as shown in FIG. 9, and the like.

Figure 14:
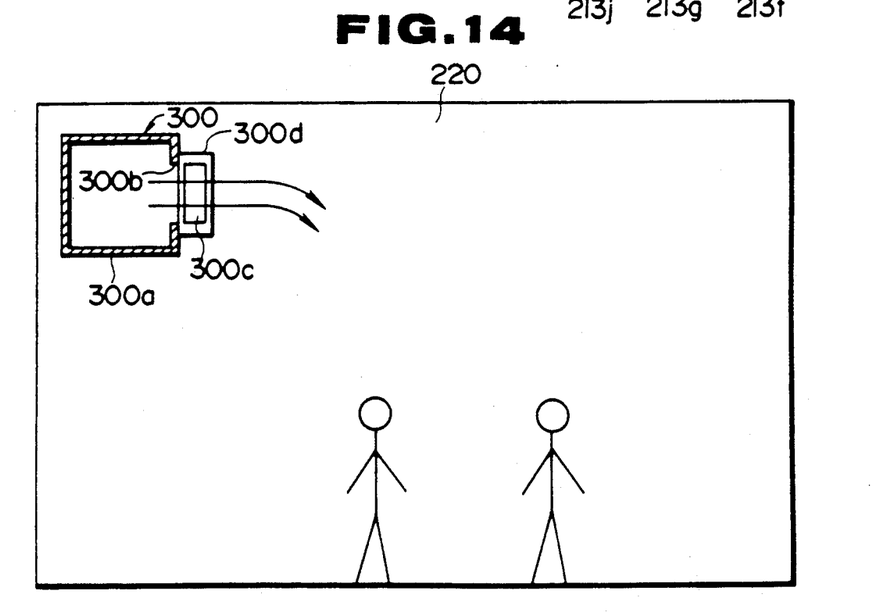
FIG. 14 is a sectional view taken on a vertical plane, showing another apparatus for supplying aromas disposed within a zone for relaxation and beauty in the facility of FIG. 11.

As seen from FIG. 14, an air conditioner 300 including a conditioner body 300a, a duct 300b for introducing a fresh or a refreshed air into the aforesaid zone 220, a cassette 300c for diffusing the aroma with the air, and a holder 300d for receiving the cassette 300c is preferably used for supplying the aroma to the zone 220. Especially, essential oils such as jasmine oil, camomile oil, neroli oil, etc., alcohols such as nonyl alcohol, decyl alcohol, phenylethyl alcohol, etc., and ethers such as methyl carbonate, ethyl carbonate, etc., can refresh after a bath, and have aesthetic effects, and therefore they are preferably used as the aroma in the cassette 300c. In the zone 220, an aroma-therapy using the aroma may be carried out, and further an acoustic-therapy may be carried out with aroma considering the product of music is multiplied by the aroma. In addition, other facilities (not shown) such as a resting room, a cafeteria, an aesthetic saloon, a beauty saloon, a boutique and the like may be disposed in the zone 220.

Also, the apparatus 1 of FIGS. 2 and 3 is disposed in the zone for heart 230. A plurality of aromatic materials used in the zone 230 include essential oils such as lavender, bergamot, marjoram, lemon, rosemary, sage, peppermint, basil, rose, jasmine, nutmeg, cinnamon, clove, ginger, etc., and compounds such as citral, citronellal, borneol, linalol, geraniol, rhodinol, nerol, etc. The zone 230 is a space for refreshing mentally, and therefore may have other facilities (not shown) such as a meditation room, a museum for aroma, and the like. Further the air conditioner 300 of FIG. 14 can of course be used in the zone 230.

The hall 240 is a terminal or an entrance and exit for the zones 210, 220 and 230. Plural facilities (not shown) such as an information counter, a locker room, cafeteria, a natural food restrant, and the like may be disposed in the hall 240.

Figure 15:
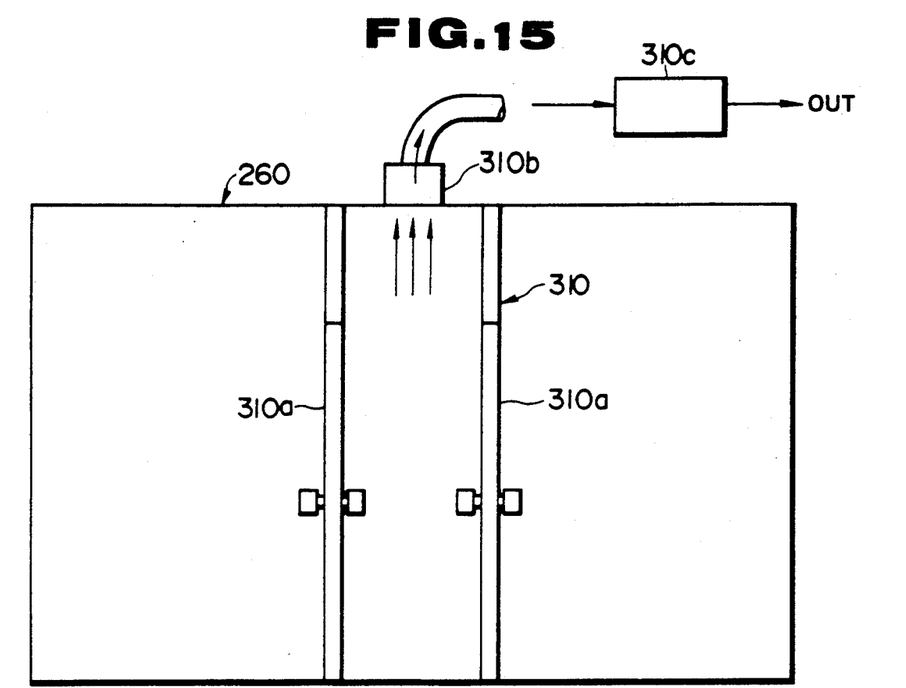
FIG. 15 is a sectional view taken on a vertical plane, showing an interceptor provided with double doors in the facility of the invention.

Plural routes 260 for linking the aforesaid zones 210, 220 and 230, and the hall 240 with each other have respectively at least an interceptor 310 for preventing ventilating between the facilities. As seen in FIG. 15, the interceptor 310 comprises double doors 310a for closing off an inner space in the routes 260, and a vacuum pump 310b for discharging the air in the space defined between the double doors 310a. The double doors 310a are not opened at the same time. Namely, when one of the door 310a is opened, another door 310a is shut. When the doors 310a are shut together, the vacuum pump 310b is turned on. Such pump 310b has an air filter 310c for filtering the air discharged from the space between the odors 310a, and thereby the air refreshed by the filter 310c is sent to the outer facilities.

Figure 16:
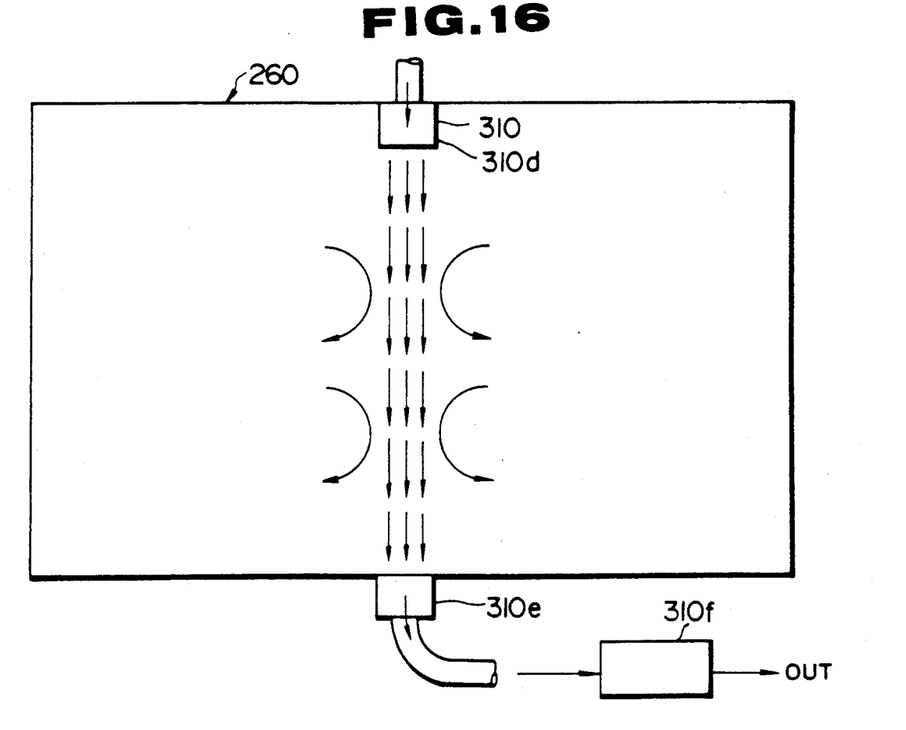
FIG. 16 is a sectional view taken on a vertical plane, showing another interceptor in the facility of the invention.

Also, as seen in FIG. 16, the interceptor 310 may be air curtain comprising a blower 310d for sending the air from the ceiling of the route 260 to the floor thereof, and a vacuum pump 310e for discharging the air sent from the blower 310d to the outer facilities. The pump 310e also has an air filter 310f for filtering the air to thereby obtain refreshed air.

Figure 17:
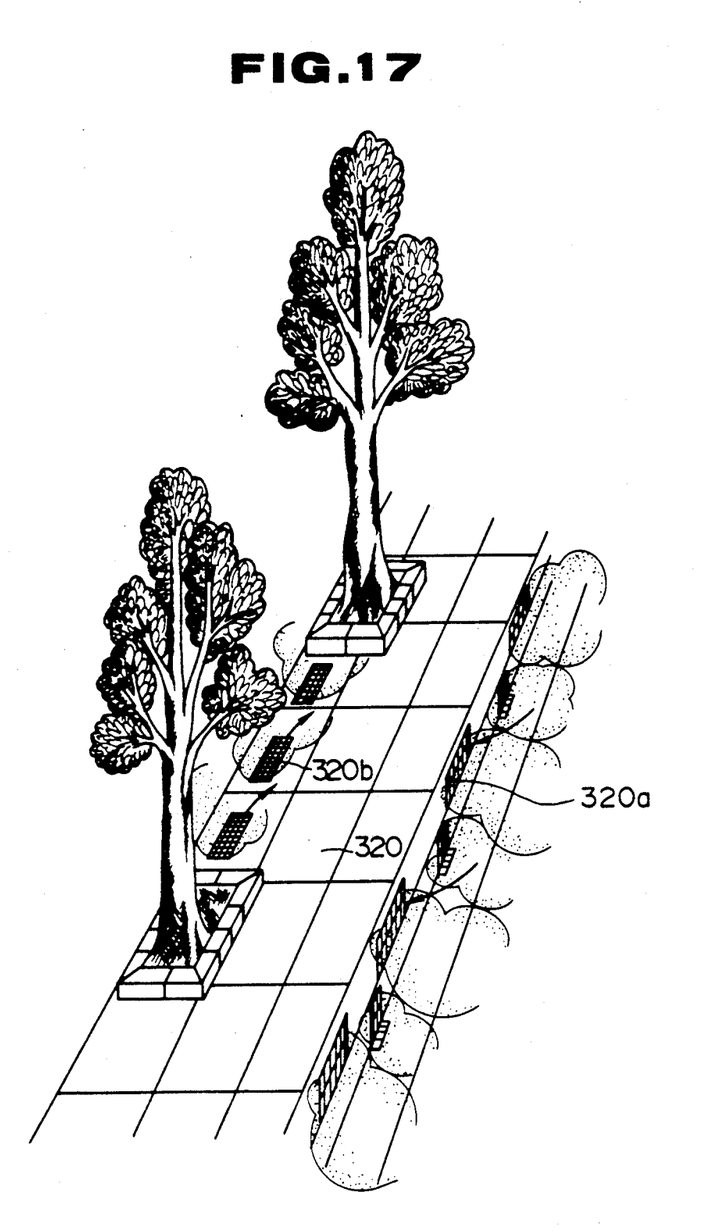
FIG. 17 is a perspective view showing an apparatus for supplying aromas of the invention which is disposed under a sidewalk.

Further the apparatus 1 of FIGS. 2 and 3 is disposed in the car-park 270 as shown in FIG. 17. Namely, the apparatus 1 is disposed under a sidewalk 320. A window 320a for introducing the air into the apparatus 1 can be disposed at the side of the sidewalk 320, and a window 320b for discharging the aromatized air can be disposed at the top wall thereof. In this case, the aroma of the air discharged by the apparatus 1 is preferably the phytoncide diffused from the trees, or the artificial aroma thereof.

The above described facilities for recuperation of the present invention can be used by a method of using them comprising the steps of checking in at the information counter, bathing in the plural baths of the health zone 210 to thereby refresh and warm up, cooling down at the relaxation and beauty zone 220, meditating at the heart zone 230, and coming back to the hall 240. When the facilities and the routes are arranged so as to be in a circular layout, the tour of the circle preferably is in a counterclockwise direction because the heart is at the left-side of the body thereof.

In the abovementioned facilities, although one zone is disposed in each building, all of the zones may be disposed in one building.

In addition, the aromatic materials supplied to such zones may be diffused by emmitting supersonic waves thereon.

What is claimed is:

1. A facility comprising:
   plural zones;
   plural routes connecting said zones with each other; and
   apparatus in each zone for supplying aromas thereto comprising: a receptor having plural aromas, a controller for controlling said receptor to select one stated aroma from said plural aromas in said receptor according to an influence on people by said stated aroma at a stated time in a day, and a ventilator connected to said receptor for supplying air containing said stated aroma to the corresponding zone.

2. An apparatus for supplying aromas comprising:
   a cylindrical receptor having plural containers for receiving aromas, each of said containers being defined by a peripheral wall and plural walls extending radially from a center thereof to said peripheral wall and having an inlet aperture and an outlet aperture for passing air therethrough, a ventilator for supplying air to the container where a selected aroma is received to obtain an air containing aroma, drive means having a drive shaft for rotating said receptor about an axis thereof so as to move a stated container to a stated position for passage of air therethrough, air passage means for interconnecting said receptor and said ventilator, and a controller for controlling said receptor to adjust the amount of one stated aroma from the plural aromas in said receptor according to an influence on people by the stated aroma at a stated time in a day.

3. A facility provided with plural apparatus for supplying aromas according to claim 2, the facility including plural zones each being provided with at least one of said apparatus, and plural routes for interconnecting said zones with each other.

4. A facility according to claim 3, further comprising a building in which all of said zones are disposed.

5. A facility according to claim 3, further comprising plural building, and at least one zone is disposed in each building.

6. A facility according to claim 3, further comprising an interceptor in each route for preventing air in said zones from free communication between said zones, said interceptor including double doors extending transversely of the respective route, a vacuum pump for exhausting the air in the space defined between said double doors to the exterior of said facility, and a controller for controlling opening and closing of said double doors so as to close one of said double doors when the other is opened.

7. A facility according to claim 3, wherein said zones are circularly arranged and communicated to each other through said routes so as to be passable in a counterclockwise direction.

8. A facility according to claim 3 including an interceptor in each route for preventing air in said zones from free communication between said zones comprising means for providing an air curtain transversely across each route.

9. An apparatus for supplying aromas according to claim 2, wherein said receptor includes a cylindrical vessel, a circular plate in said vessel having plural apertures opened at regular intervals at the marginal portion along the peripheral edge of said plate, plural cylindrical cassettes having opposite ends for retaining plural aroma-carriers therein, each of said cassettes being housed in a respective aperture in said plate, and a pair of screen sheets having plural perforations for covering the opposite ends of the cassettes while permitting the passing of air therethrough.

10. An apparatus for supplying aromas according to claim 9, wherein the aroma-carriers are beads having aromas adhered to the surfaces thereof.

11. An apparatus for supplying aromas according to claim 9, wherein the aroma-carriers are sponges containing liquid aroma therein.

* * * * *